United States Patent
Tortelli et al.

(10) Patent No.: US 7,208,638 B2
(45) Date of Patent: *Apr. 24, 2007

(54) PROCESS FOR PREPARING FLUOROHALOGENETHERS

(75) Inventors: Vito Tortelli, Milan (IT); Stefano Millefanti, Como (IT); Pierangelo Calini, Milan (IT)

(73) Assignee: Solvay Solexis, S.p.A., Milan (IT)

( * ) Notice: Subject to any disclaimer, the term of this patent is extended or adjusted under 35 U.S.C. 154(b) by 140 days.

This patent is subject to a terminal disclaimer.

(21) Appl. No.: 11/044,022

(22) Filed: Jan. 28, 2005

(65) Prior Publication Data

US 2005/0171388 A1    Aug. 4, 2005

(30) Foreign Application Priority Data

Dec. 3, 2004    (IT) .............................. MI04A0133

(51) Int. Cl.
C07C 41/18    (2006.01)

(52) U.S. Cl. ...................................... 568/615; 562/849
(58) Field of Classification Search ................ 568/615; 562/849
See application file for complete search history.

(56) References Cited

U.S. PATENT DOCUMENTS

| | | | |
|---|---|---|---|
| 3,242,218 A | 3/1966 | Miller | |
| 3,715,378 A | 2/1973 | Sianesi et al. | |
| 3,810,874 A | 5/1974 | Mitsch et al. | |
| 3,847,978 A | 11/1974 | Sianesi et al. | |
| 4,523,039 A | 6/1985 | Lagow et al. | |
| 4,647,413 A | 3/1987 | Savu | |
| 4,755,300 A | 7/1988 | Fischel et al. | |
| 4,788,257 A | 11/1988 | Caporiccio et al. | |
| 4,801,409 A | 1/1989 | Marraccini et al. | |
| 4,816,599 A | 3/1989 | Gregorio et al. | |
| 4,827,024 A | 5/1989 | Guglielmo et al. | |
| 4,900,872 A | 2/1990 | Guglielmo et al. | |
| 4,906,770 A | 3/1990 | Marchionni et al. | |
| 4,962,282 A | 10/1990 | Marraccini et al. | |
| 5,149,842 A | 9/1992 | Sianesi et al. | |
| 5,225,576 A | 7/1993 | Navarrini et al. | |
| 5,258,110 A | 11/1993 | Sianesi et al. | |
| 6,835,856 B2 * | 12/2004 | Tortelli et al. ............... | 568/615 |
| 7,019,177 B2 * | 3/2006 | Tortelli et al. ............... | 568/615 |

FOREIGN PATENT DOCUMENTS

| | | |
|---|---|---|
| EP | 0 148 482 A2 | 7/1985 |
| EP | 0 239 123 A2 | 9/1987 |
| EP | 0 340 740 A2 | 11/1989 |
| EP | 1 333 020 A2 | 8/2003 |
| EP | 1 388 531 A1 | 2/2004 |
| GB | 1104482 | 2/1968 |
| WO | WO 90/03357 A1 | 4/1990 |

OTHER PUBLICATIONS

Carl G. Krespan, "Fragmentation of Fluorosulfonyldifluoroaceltyl Fluoride Induced by Fluoride Ion," Journal of Fluorine Chemistry, 16, 1980, pp. 385-390.
Walter Navarrini et al., "Organic Hypofluorites and Their New Role in Industrial Fluorine Chemistry," Journal of Fluorine Chemistry 95, 1999, pp. 27-39.

* cited by examiner

*Primary Examiner*—Rosalynd Keys
(74) *Attorney, Agent, or Firm*—Arent Fox LLP

(57) ABSTRACT

A process for preparing (per)fluorohalogenethers having general formula:

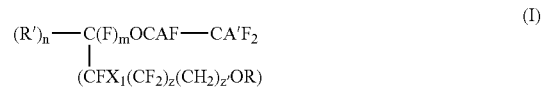

wherein:
A and A', equal to or different from each other, are selected among Cl, Br and H; m=1, 2; n=0, 1; R' is a $C_1$ to $C_3$ (per)fluoroalkyl substituent; R is a (per)fluoropolyether substituent; z and z' are 1 or zero, $X_1$=F, $CF_3$;
by reaction of carbonyl compounds having formula:

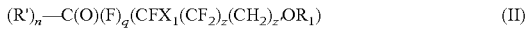

wherein:
R' and n are as above; q=0, 1; $X_1$=F or $CF_3$; z=0 or 1;
$R_1$ is a (per)fluoropolyether substituent;
in liquid phase, with elemental fluorine and with olefinic compounds of formula:

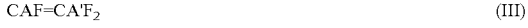

wherein A and A' are as above,
at temperatures from −120° C. to −20° C., preferably from −100° C. to −40° C.

14 Claims, No Drawings

PROCESS FOR PREPARING FLUOROHALOGENETHERS

The present invention relates to a process for preparing fluorinated vinylethers having (per)fluoro-polyether structure.

More specifically the present invention relates to the preparation of fluorohalogenethers having a (per)fluoropolyether structure which by dehalogenation or dehydrohalogenation give fluorinated vinylethers. The process of the invention allows to obtain fluorohalogenethers having a (per)fluoropolyether structure by a reaction wherein no catalysts are used, maintaining a good selectivity.

As known, the fluorinated vinylethers form a class of valuable monomers for obtaining various polymers, from fluorinated elastomers to thermoprocessable semicrystalline fluorinated polymers.

Processes for obtaining fluorohalogenethers using the reaction of hypofluorites with olefins are known in the prior art. For the hypofluorite preparation the most known processes use metal fluorides-based catalysts.

In U.S. Pat. No. 4,827,024 it is described the preparation in a continuous way of hypofluorites, by fluorination, in equimolecular amounts, with fluorine of halogenated carbonyl compounds having at least two carbon atoms, in the presence of catalysts formed of CsF, optionally in admixture with metals as, for example, copper. Generally these metals are used, besides as catalyst (CsF) supports, also to make the thermal exchange easier, i.e. to dissipate the heat generated in the hypofluorite synthesis.

The metal support according to the above prior art must accomplish two main functions: 1) to maintain the catalyst in a form accessible to the reactants, 2) to facilitate the thermal exchange maintaining controllable in the required range the temperature of the catalytic bed. Further and essential feature of the support is the complete inertia towards the reactants and reaction products.

In U.S. Pat. No. 4,816,599, U.S. Pat. No. 4,801,409 and U.S. Pat. No. 4,962,282 hypofluorites are preferably prepared by using an excess of fluorine to completely convert the acylfluoride into hypofluorite so that the acylfluoride concentration on the catalytic bed is very low, since it is known that some acylfluorides give rise to decomposition reactions in the presence of CsF. See for example Carl G. Krespan in Journal of Fluorine Chemistry, 16 (1980) 385–390.

Tests carried out by the Applicant on the processes of the prior art for preparing hypofluorites, by using the above described catalysts, have shown that by using said catalytic systems, both in a discontinuous and continuous way, the catalytic activity is rapidly reduced in the time. The Applicant has found in particular that the activity reduction is very marked, until complete catalyst deactivation, when in the hypofluorite synthesis an excess of fluorine on the stoichiometric value is used, condition indicated as preferred in the described processes of the prior art.

According to the prior art one must therefore operate in excess of fluorine in the hypofluorite synthesis to reduce as much as possible the above described inconveniences. By operating under said conditions the prior art catalyst deactivates very rapidly, in about two-three days. With so low durations it is in practice impossible to have available a continuous industrial plant.

Furthermore, in the hypofluorite synthesis processes in a discontinuous way, when the catalytic bed is used in the absence of support, its further use in the reaction for obtaining hypofluorites brings to very low yields and a very rapid deactivation is observed.

Processes to obtain fluorinated vinylethers are known in the prior art. U.S. Pat. No. 4,900,872 describes the preparation of perfluorovinylether precursors, by continuous reaction between perfluoroalkyl hypofluorites diluted in an inert solvent and an olefin having formula $CA'F=CA'^{'}F$, wherein A and A', equal to or different from each other, are Cl and Br. In the patent it is indicated that said hypofluorites can be directly fed from the reactor wherein their synthesis takes place in gaseous phase, by reaction of fluorine with acylfluoride on catalyst. The obtained products are converted into perfluorovinylethers by dehalogenation with zinc. In this process the drawbacks are those above reported as regards the hypofluorite preparation. In particular the drawback of said processes resides in that one has to synthesize and immediately use the hypofluorites, which, as known, are unstable compounds, in particular when the number of carbon atoms in the hypofluorite perfluoroalkyl chain is higher than or equal to 2. Besides, in the hypofluorite synthesis it is known that a catalyst must be used, with the above drawbacks.

In U.S. Pat. No. 5,225,576 the reaction between hypofluorite and a (per)halo-olefin for preparing (per)haloethers is carried out by flowing a gaseous phase, containing the hypofluorite, in the liquid phase containing the (per)haloolefin maintained at low temperature. To obtain high yields of the sum reaction, it is necessary to work at a low temperature. Under these conditions however a partial hypofluorite condensation can take place, before the hypofluorite comes into contact with the olefin. This leads to the hypofluorite decomposition and therefore explosions can be caused. For example the hypofluorite $CF_3CF_2CF_2OF$ having a molecular weight 204 has a boiling point of –9° C. (Journal of fluorine Chemistry, Vol. 95 (1999) 29) and can easily condensate at the temperatures used in the (per)haloether synthesis. At temperatures lower than –30° C. the process of the above patent is applicable only to hypofluorites having a low boiling point, i.e. having 1 or 2 carbon atoms in the chain.

U.S. Pat. No. 4,906,770 describes hypofluorites of formula $Rf^1OCF_2OF$ and $FOCF_2ORf^1OCF_2OF$, wherein $Rf^1$ is a perfluoropolyether radical, even of high molecular weight, and the respective addition products with olefins. The process for preparing said hypofluorites requires a peroxide fluorination with UV light at temperatures in the range from –60 to 30° C. The reaction times are very long and the conversion into hypofluorite, when it is complete, determines low hypofluyorite yields. See the Examples. Furthermore the use of the UV light is expensive in an industrial process.

U.S. Pat. No. 4,801,409 describes the preparation of bis hypofluorites of general formula $FOCF_2—Rf^3—CF_2OF$ in gaseous phase. $Rf^3$ is a perfluoroalkylene or perfluorooxyalkylene. The only Example of hypofluorite having a number of carbon atoms higher than two is a hypofluorite having three carbon atoms. Tests carried out by the Applicant have shown that with these hypofluorites very low yields of addition to olefins are obtained.

In the prior art the hypofluorite synthesis with a number of carbon atoms higher than two is carried out at temperatures from 0° C. to 60° C., in particular at 20° C. in gaseous phase, to avoid the condensation and thus explosions. Furthermore very high dilutions of the acylfluoride precursor are used. See U.S. Pat. No. 4,801,409.

EP 1,333,020 describes a process having high yields for the synthesis of (per)haloethers obtained from hypofluorites having a number of carbon atoms higher than 2, by using also hypofluorites having a high molecular weight. The (per)haloethers can have (per)fluoroalkyl and oxy(per)-fluoroalkyl chain; besides they can be mono or bifunctional depending on the use of mono or bis-hypofluorite precursors. In the process described in EP 1,333,020, which can be in continuous, semi-continuous or discontinuous, hypofluorites at high concentrations, even without solvent, and catalysts of formula MeFy.zHF for their synthesis from acylfluorides are used. The drawbacks of this process are the same previously mentioned connected with the catalyst and the hypofluorite use.

The need was felt to have available a process for preparing fluorohalogenethers, avoiding the drawbacks of the prior art, and maintaining a good selectivity.

An object of the present invention is a process for preparing (per)fluorohalogenethers having general formula:

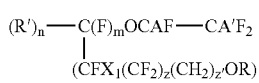
$$(R')_n—C(F)_mOCAF—CA'F_2$$
$$|$$
$$(CFX_1(CF_2)_z(CH_2)_{z'}OR)$$
(I)

wherein:
A and A', equal to or different from each other, are selected from Cl, Br and H, with the proviso that A and A' are not contemporaneously equal to H;
m=1, 2;
n=0, 1;
with the proviso that when m=2, n=0 and when m=1, n=1;
R' is a (per)fluoroalkyl substituent containing from 1 to 3 carbon atoms;
$X_1$=F, $CF_3$;
z=0, 1;
z'=0, 1;
R is a (per)fluoropolyether substituent having formula $—R_f-T$, wherein T has the following meanings:

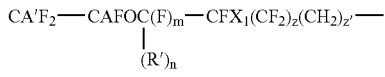
$$CA'F_2—CAFOC(F)_m—CFX_1(CF_2)_z(CH_2)_{z'}—$$
$$|$$
$$(R')_n$$

wherein A, A', R', m, n, $X_1$, z and z' are as above;
$X_I CFX_1 (CF_2)_z (CH_2)_{z'}—$
wherein $X_I$=F, $CF_3$, Cl; $X_1$, z and z' are as above;

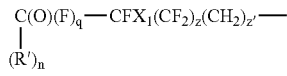
$$C(O)(F)_q—CFX_1(CF_2)_z(CH_2)_{z'}—$$
$$|$$
$$(R')_n$$

wherein R' and n are as above; $X_1$, z and z' are as above;
q=0, 1 with the proviso that when q=0 then n=1; when q=1 then n=0;
$R_f$ is a (per)fluorooxyalkylene chain containing one or more of the following units statistically distributed along the chain:
$(C_3F_6O)$;
$(CFX_1O)$ wherein $X_1$ is F or $CF_3$;
$(C_2F_4O)$;
$(CF_2(CF_2)_{x'}CF_2O)$ wherein x' is an integer equal to 1 or 2;
$(CR_4R_5CF_2CF_2O)$ wherein $R_4$ and $R_5$ are equal to or different the one from the other and are selected between H, Cl, and one fluorine atom of the perfluoromethylene unit can optionally be substituted with H, Cl or (per)fluoroalkyl having, for example, from 1 to 4 carbon atoms;

by reaction of carbonyl compounds having formula:

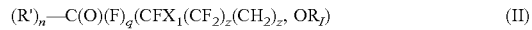
$$(R')_n—C(O)(F)_q(CFX_1(CF_2)_z(CH_2)_{z'} OR_I)$$
(II)

wherein:
R', n, $X_1$, z and z' are as above defined;
q=0, 1;
$R_I$ is a (per)fluoropolyether substituent $-R_f T_I$ wherein:
$R_f$ is as above,
$T_I$ has the following meanings:
$X_I CFX_1(CF_2)_z(CH_2)_{z'}-$, wherein $X_I$, $X_1$, z and z' are as above,
$(R')_n—C(O)(F)_q—CFX_1(CF_2)_z(CH_2)_{z'}—$
wherein:
R', n, q, $X_1$, z and z' are as above;
with the proviso that when q=0 then n=1; when q=1 then n=0;

in liquid phase, with elemental fluorine and with olefinic compounds of formula:

$$CAF=CA'F_2$$ (III)

wherein A and A' are as above, at temperatures from −120° C. to −20° C., preferably from −100° C. to −40° C., optionally in the presence of an inert solvent under the reaction conditions.

The number average molecular weight of $R_f$ in formula (I) and (II) ranges from 66 to 12,000. Preferably from 66 to 1,000, more preferably from 300 to 800.

The $(C_3F_6O)$ unit of $R_f$ is selected between $(CF_2CF(CF_3)O)$ or $(CF(CF_3)CF_2O)$.

The perfluorooxyalkykene chains $R_f$ are selected, for example, from the following:

(a') $—(CF_2CF_2O)_{p'}(CF_2O)_{q'}$ when $R_f$ has the meaning of (a') in the formulas (I) and (II) z=z'=0, $X_1$=F;
in formula (a'):
p' and q' are numbers such that the q'/p' ratio is between 0.2 and 4, p' being different from zero; and
the number average molecular weight is within the above range;

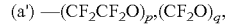
(b') $—(CF_2CF(CF_3)O)_{r'}—(CF_2CF_2O)_{s'}—(CFX_1O)_{t'}—$ when $R_f$ has the meaning of (b') in the formulas (I) and (II) z=z'=0, $X_1$=F, $CF_3$;
in formula (b'):
$X_1$ is as above; r', s' and t' are numbers such that r'+s' is between 1 and 50, the t'/(r'+s') ratio is between 0.01 and 0.05, r'+s' being different from zero, and the molecular weight is within the above range;

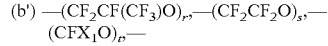
(c') $—(CF_2CF(CF_3)O)_{u'}-R'_fO—(CF(CF_3)CF_2O)_{u'}—$ when $R_f$ has the meaning of (c') in the formulas (I) and (II) z=z'=0, $X_1$=$CF_3$;
in formula (c'):
$R'_f$ is a $C_1$-$C_3$ perfluoroalkyl bifunctional radical;
u' is a number such that the number average molecular weight is within the above range;

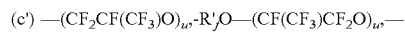
(c") $(CFX_1O)_{r'}—((CF_3)FCF_2O)_{r'}—R'_fO—(CF_2CF(CF_3)O)_{r'}-(CFX_1O)_{r'}—$ when $R_f$ has the meaning of (c") in the formulas (I) and (II) z=z'=0, $X_1$=F, $CF_3$;

in formula (c''):

R'$_f$ is a C$_1$-C$_3$ perfluoroalkyl bifunctional radical; r', t' and X$_1$ are as above; r' and t' such that the number average molecular weight is within the above range;

(d') —(CF$_2$(CF$_2$)$_{x'}$CF$_2$O)$_{v'}$— when R$_f$ has the meaning of (d') in the formulas (I) and (II) z=1, z'=0, X$_1$=F;
in formula (d'):
v' is a number such that the molecular weight is within the above range, x' is an integer equal to 1 or 2;

(e') —(CF$_2$CF$_2$CH$_2$O)$_{w'}$-R'$_f$O—(CH$_2$CF$_2$CF$_2$O)$_{w'}$— when R$_f$ has the meaning of (e') in the formulas (I) and (II) z=0, z'=1, X$_1$=F;
in formula (d'):
R'$_f$ is as above; w' is a number such that the number average molecular weight is within the above range.

Preferably R$_f$ has structure (a').

The (per)fluoropolyoxyalkylenes can be prepared starting from the corresponding (per)fluoropolyoxyalkylenes having —COF end groups. See for example the patents GB 1,104,482, U.S. Pat. No. 3,715,378, U.S. Pat. No. 3,242,218, U.S. Pat. No. 4,647,413, EP 148,482, U.S. Pat. No. 4,523,039, EP 340,740, patent application WO 90/03357, U.S. Pat. No. 3,810,874, EP 239,123, U.S. Pat. No. 5,149,842, U.S. Pat. No. 5,258,110.

The fluorine used in the reaction can optionally be diluted with an inert gas such as nitrogen or helium.

The process according to the present invention is carried out in a sole reactor and the reaction can be carried out in a semicontinuous or continuous way.

The semicontinuous process can, for example, be carried out by feeding gaseous fluorine into the reactor containing the carbonyl compounds of formula (II) and the olefinic compounds of formula (III). The molar ratio (II)/(III) can range in a wide range, for example between 0.05 and 10. The fluorine feed is continued until complete olefin conversion. This condition can be easily determined when the exothermy of the reaction is no longer noticed. Indeed by carrying out the reaction of the compounds (II) and (III) for example at −100° C., as soon as the reaction compounds react with the elemental fluorine, there is exothermy and the temperature increases of about 5–°15° C. Therefore the reaction ends when, for example, the compound (III) has been completely consumed. At this point the reactor temperature returns to the initial value.

In the continuous process the gaseous fluorine and the compounds (II) and (III) are fed into the reactor, until reaching the steady state. In practice the reactants are fed into the reactor with fixed flow-rates and the reaction mixture is continuously drawn. The steady state is reached when the concentrations of the three reactants and of the reaction products in the reactor are equal to the concentration of the reactants and reaction products flowing out from the reactor.

The molar ratios between the reactants are not particularly binding, for example the molar ratio (II)/(III) can range from 0.05 to 10 and F$_2$/(III) from 0.05 to 10.

As solvents in the process of the present invention, compounds liquid and inert, in the above temperature range, can be used. Compounds selected, for example, from (per)fluorocarbons, (per)fluoroethers, (per)fluoropolyethers, perfluoroamines, or respective mixtures, can be used. The skilled in the field is able to select in the above classes the compounds to be used as solvents on the basis of their physical properties.

The precursors of the carbonyl compounds of formula (II) can be prepared according to various methods. The synthesis processes described in U.S. Pat. No. 4,788,257, U.S. Pat. No. 4,755,300, U.S. Pat. No. 3,847,978 can, for example, be used.

The conversion of the fluorohalogenethers of formula (I) into the corresponding vinylethers with —OCF=CF$_2$ end groups can be carried out by the known dehalogenation and dehydrohalogenation methods of the prior art.

As said, with the process of the present invention fluorinated monovinylethers are obtainable wherein the other end group contains a carbonyl group.

The following Examples are given for illustrative and non limitative purposes of the present invention.

EXAMPLES

Example 1

Synthesis of Fluorohalogenethers by Using a Mixture of Perfluoropolyether Diacyl Fluorides Having Structure F(O)C—CF$_2$—O—(CF$_2$CF$_2$O)t-(CF$_2$O)p—CF$_2$—COF A sample of 14 g of a perfluoropolyether diacylfluoride having structure F(O)C—CF$_2$—O—(CF$_2$CF$_2$O)t-(CF$_2$O)p—CF$_2$—COF, wherein t and p are such that the number average molecular weight is 407, is fed into a 50 cm$^3$ glass reactor equipped with stirrer and two bubbling inlets for the fluorine and CFC 1112 (CFCl=CFCl) feeding. The reaction is carried out at −70° C. by feeding 1.7 Nl/h of fluorine diluted with 4.2 Nl/h of helium (molar ratio helium/fluorine=2.5/1) and CFC 1112 with flow-rate equal to 1.6 Nl/h, for 4 h.

The material balance at the end of the reaction is 95%. The reaction raw product is distilled at 40° C. at the head to separate the light components, identified by gaschromatographic analysis as CFC 114 and CFC 113, which are by-products formed in the reaction. The distillation residue is characterized by gaschromatography and $^{19}$F NMR. The conversion of the —COF end groups is 99% and that of CFC 1112 is quantititave.

The selectivity to —OCFCl—CF$_2$Cl end groups referred to the —COF equivalents is 65%. The selectivity referred to the —COF equivalents is divided in the various molecules as follows:

59% to the —OCFCl—CF$_2$Cl end groups of the bis-adduct CF$_2$Cl—CFCl—O—CF$_2$—CF$_2$—O—(CF$_2$CF$_2$O)t-(CF$_2$O)p-CF$_2$—CF$_2$—O—CFCl—CF$_2$Cl;

1% to the —OCFCl—CF$_2$Cl end groups of the mono-adduct CF$_2$Cl—CFCl—O—CF$_2$—CF$_2$—O—(CF$_2$CF$_2$O)t-(CF$_2$O)p—CF$_2$—COF;

5% to the —OCFCl—CF$_2$Cl end groups of molecules CF$_2$Cl—CFCl—O—CF$_2$—CF$_2$—O—(CF$_2$CF$_2$O)t-(CF$_2$O)p—CF$_3$.

The diacylfluoride conversion is of 100% and the respective selectivity to bis-adduct and mono-adduct are 55.3% and 1.1% respectively.

Example 2

Synthesis of Fluorohalogenethers by Using a Mixture of Perfluoropolyether Diacyl Fluorides Having Structure F(O)C—CF$_2$—O—(CF$_2$CF$_2$O)t-(CF$_2$O)p—CF$_2$—COF The Example 1 is repeated by feeding with the same flow-rate fluorine and CFC 1112 (CFCl=CFCl) for 1 hour.

The material balance is 94%. The reaction raw product is distilled at 40° C. at the head to separate the light components, which the gaschromatographic analysis shows to be formed of unreacted CFC 1112, CFC 114 and CFC 113, by-products of the reaction.

The distillation residue is characterized by gaschromatography and $^{19}$F NMR. The conversion of the —COF end groups is 64.0%, that of CFC 1112 is 98%.

The residual raw product is then salified up to a basic pH with an aqueous solution at 15% of KOH and a distillation in steam current is carried out to remove the neutral mixture components and isolate the unreacted diacylfluoride and the mono-adduct. Two fractions are obtained from which the organic phases are separated from the aqueous phases, by analyzing the organic phase by $^{19}$F NMR. The distillation balance is 97%. The distillation residue in steam current, containing the potassium salts of the acid derivatives, is analyzed by $^{19}$F NMR.

The selectivity to —OCFCl—CF$_2$Cl end groups referred to the —COF equivalents is 78.0%. Said slectivity referred to the —COF equivalents is divided in the various molecules as follows:

20% to the —O—CFCl—CF$_2$Cl end groups of the bis-adduct CF$_2$Cl—CFCl—O—CF$_2$—CF$_2$—O—(CF$_2$CF$_2$O)t-(CF$_2$O)p-CF$_2$—CF$_2$—O—CFCl—CF$_2$Cl;

53% to the —OCFCl—CF$_2$Cl end groups of the mono-adduct CF$_2$Cl—CFCl—O—CF$_2$—CF$_2$—O—(CF$_2$CF$_2$O)t-(CF$_2$O)p—CF$_2$—COF;

5% to the —OCFCl—CF$_2$Cl end groups of compounds

CF$_2$Cl—CFCl—O—CF$_2$—CF$_2$—O—(CF$_2$CF$_2$O)t-(CF$_2$O)p—CF$_3$.

The diacylfluoride conversion is 100% and the respective selectivities to bis-adduct and mono-adduct are 9.9% and 52.9% respectively.

The invention claimed is:

1. A process of preparing (per)fluorohalogenethers having general formula:

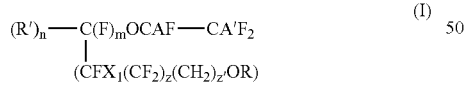
(I)

wherein:
A and A', equal to or different from each other, are selected among Cl, Br and H, with the proviso that A and A' are not contemporaneously equal to H;
m=1 or 2;
n=0 or 1;
with the proviso that when m=2, n=0 and when m=1, n=1;
R' is a (per)fluoroalkyl substituent containing from 1 to 3 carbon atoms;
X$_1$=F or CF$_3$;
z=0 or 1;
z' =0 or 1;

R is a (per)fluoropolyether substituent having formula -R$_f$T, wherein T has the following meanings:

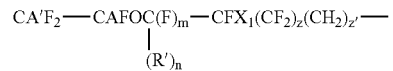

wherein A, A', R', m, n, X$_1$, z and z' are as above;

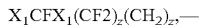

wherein X$_1$=F, CF$_3$, Cl; X$_1$, z and z' are as above;

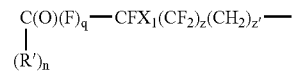

wherein R' and n are as above; X$_1$, z and z' are as above;
q=0, 1 with the proviso that when q=0 then n=1; when q=1 then n=0;
R$_f$ is a (per)fluorooxyalkylene chain containing one or more of the following units statistically distributed along the chain:
(C$_3$F$_6$O);
(CFX$_1$O) wherein X$_1$ is F or CF$_3$;
(C$_2$F$_4$O);
(CF$_2$(CF$_2$)$_{x'}$CF$_2$O) wherein x' is an integer equal to 1 or 2;
(CR$_4$R$_5$CF$_2$CF$_2$O) wherein R$_4$ and R$_5$ are equal to or different the one from the other and are selected between H, Cl, and one fluorine atom of the perfluoromethylene unit can optionally be substituted with H, Cl or (per)fluoroalkyl having, for example, from 1 to 4 carbon atoms;
by reaction of carbonyl compounds having formula:

(R')$_n$—C(O)(F)$_q$(CFX$_1$(CF$_2$)$_z$(CH$_2$)$_{z'}$OR$_1$)   (II)

wherein:
R', n, X$_1$, z and z' are as above;
q=0, 1;
R$_1$ is a (per)fluoropolyether substituent -R$_f$T$_1$
wherein:
R$_f$ is as above,
T$_1$ has the following meanings:
X$_1$CFX$_1$(CF$_2$)$_z$(CH$_2$)$_{z'}$—, wherein X$_1$X$_1$, z and z' are as above,
(R')$_n$—C(O)(F)$_q$—CFX$_1$(CF$_2$)$_z$(CH$_2$)$_{z'}$—
wherein: R', n, q, X$_1$, z and z' are as above;
with the proviso that when q=0 then n=1; when q=1 then n=0;

in liquid phase, with elemental fluorine and with olefinic compounds of formula:

CAF=CA'F$_2$   (III)

wherein A and A' are as above,
at temperatures from −120° C. to −20° C., optionally in the presence of an inert solvent under the reaction conditions.

2. A process according to claim 1, wherein the number average molecular weight of R$_f$ in formula (I) and (II) ranges from 66 to 12,000.

3. A process according to claim 1, wherein (C$_3$F$_6$O) unit of R$_f$ is selected between (CF$_2$CF(CF$_3$)O) or (CF(CF$_3$)CF$_2$O).

4. A process according to claim 1, wherein the perfluorooxyalkylene chains Rf are selected from the following:

(a') —$(CF_2CF_2O)_{p'}(CF_2O)_{q'}$—
  when $R_f$ has the meaning of (a') in the formulas (I) and (II) z=z'=0,
  $X_1$=F;
  in formula (a'):
  p' and q' are numbers such that the q'/p' ratio is between 0.2 and 4, p' being different from zero; and the number average molecular weight is within the above range;

(b') —$(CF_2CF(CF_3)O)_{r'}$—$(CF_2CF_2O)_{s'}$—$(CFX_1O)_{t'}$—
  when $R_f$ has the meaning of (b') in the formulas (I) and (II) z=z'=0,
  $X_1$=F, $CF_3$;
  in formula (b'):
  $X_1$ is as above; r', s' and t' are numbers such that r'+s' is between 1 and 50, the t'/(r'+s') ratio is between 0.01 and 0.05, r'+s' being different from zero, and the molecular weight is within the above range;

(c') —$(CF_2CF(CF_3)O)_{u'}$—$R'_fO$—$(CF(CF_3)CF_2O)_{u'}$—
  when Rf has the meaning of (c') in the formulas (I) and (II) z=z'=0,
  $X_1$=$CF_3$;
  in formula (c'):
  $R'_f$ is a $C_1$–$C_3$ perfluoroalkyl bifunctional radical;
  u' is a number such that the number average molecular weight is within the above range;

(c") $(CFX_1 O)_{t'}$—$((C F_3)CFCF_2O)_{r'}$—$R'_fO$—$(CF_2CF(CF_3)O)_{r'}$—$(CFX_1O)_{t'}$—
  when $R_f$ has the meaning of (c") in the formulas (I) and (II) z=z'=0,
  $X_1$=F, $CF_3$;
  in formula (c"):
  $R'_f$ is a $C_1$–$C_3$ perfluoroalkyl bifunctional radical; r', t' and $X_1$ are as above;
  r' and t' such that the number average molecular weight is within the above range;

(d') —$(CF_2(CF_2)_xCF_2O)_{v'}$—
  when $R_f$ has the meaning of (d') in the formulas (I) and (II) z=1, z'=0,
  $X_1$=F;
  in formula (d'):
  v' is a number such that the molecular weight is within the above range,
  x' is an integer equal to 1 or 2;

(e') —$(OCF_2CF_2CH_2)_{w'}$—$R'_fO$—$(CH_2CF_2CF_2O)_{w'}$—
  when Rf has the meaning of (e') in the formulas (I) and (II) z=0, z'=1,
  $X_1$=F;
  in formula (d'):
  $R'_f$ is as above; w' is a number such that the number average molecular weight is within the above range.

5. A process according to claim 4, wherein Rf has structure (a').

6. A process according to claim 1, wherein the fluorine used in the reaction is diluted with an inert gas.

7. A process according to claim 1, carried out in a sole reactor in a semicontinuous or continuous way.

8. A process according to claim 7, wherein in the semicontinuous process the molar ratio (II)/(III) ranges from 0.05 to 10.

9. A process according to claim 7, wherein in the continuous process the molar ratio (II)/(III) ranges from 0.05 to 10 and F21 (Ill) from 0.05 to 10.

10. A process according to claim 1, wherein as solvents compounds selected from (per)fluorocarbons, (per)fluoroethers, (per)fluoropolyethers, perfluoroamines, or respective mixtures, are used.

11. A process according to claim 1, wherein the fluorohalogenethers of formula (I) are converted into the corresponding vinylethers with —OCF=$CF_2$ end groups by dehalogenation or dehydrohalogenation methods.

12. A process according to claim 1, wherein the process occurs at temperatures from −100° C. to −40° C.

13. A process according to claim 1, wherein the number average of molecular weight of $R_f$ in formula (I) and (II) ranges from 66 to 1,000.

14. A process according to claim 1, wherein the number average of molecular weight of $R_f$ in formula (I) and (II) ranges from 300 to 800.

* * * * *